(12) United States Patent
Fehre et al.

(10) Patent No.: US 8,870,750 B2
(45) Date of Patent: Oct. 28, 2014

(54) IMAGING METHOD FOR MEDICAL DIAGNOSTICS AND DEVICE OPERATING ACCORDING TO THIS METHOD

(75) Inventors: Jens Fehre, Hausen (DE); Rainer Kuth, Höchstadt (DE)

(73) Assignee: Siemens Aktiengesellschaft, Munich (DE)

( * ) Notice: Subject to any disclaimer, the term of this patent is extended or adjusted under 35 U.S.C. 154(b) by 1270 days.

(21) Appl. No.: 12/147,660

(22) Filed: Jun. 27, 2008

(65) Prior Publication Data

US 2009/0005641 A1    Jan. 1, 2009

(30) Foreign Application Priority Data

Jun. 28, 2007   (DE) .......................... 10 2007 029 888

(51) Int. Cl.
| | | |
|---|---|---|
| *A61B 1/00* | (2006.01) | |
| *A61B 1/04* | (2006.01) | |
| *A61B 1/06* | (2006.01) | |
| *A61B 6/12* | (2006.01) | |
| *A61B 19/00* | (2006.01) | |
| *A61B 5/06* | (2006.01) | |

(52) U.S. Cl.
CPC ......... *A61B 19/52* (2013.01); *A61B 2019/5289* (2013.01); *A61B 6/12* (2013.01); *A61B 5/06* (2013.01); *A61B 2019/5238* (2013.01)
USPC ............ 600/117; 600/118; 600/103; 600/160

(58) Field of Classification Search
USPC .................. 600/103, 117, 118, 424, 160, 109
See application file for complete search history.

(56) References Cited

U.S. PATENT DOCUMENTS

| | | | | |
|---|---|---|---|---|
| 5,704,897 | A * | 1/1998 | Truppe .......................... | 600/117 |
| 6,368,269 | B1 * | 4/2002 | Lane .............................. | 600/126 |
| 6,442,417 | B1 * | 8/2002 | Shahidi et al. ................ | 600/429 |
| 6,661,571 | B1 * | 12/2003 | Shioda et al. .................. | 359/372 |
| 6,768,496 | B2 | 7/2004 | Bieger et al. | |
| 6,892,090 | B2 | 5/2005 | Verard et al. | |
| 7,542,791 | B2 | 6/2009 | Mire et al. | |
| 7,967,742 | B2 * | 6/2011 | Hoeg et al. ..................... | 600/103 |
| 8,090,174 | B2 * | 1/2012 | Navab ............................ | 382/128 |
| 2004/0024310 | A1 * | 2/2004 | Graumann et al. ............ | 600/424 |
| 2004/0210105 | A1 | 10/2004 | Hale et al. | |
| 2005/0054895 | A1 * | 3/2005 | Hoeg et al. ..................... | 600/117 |
| 2005/0113809 | A1 * | 5/2005 | Melkent et al. .................... | 606/1 |
| 2005/0187432 | A1 * | 8/2005 | Hale et al. ...................... | 600/117 |
| 2007/0208252 | A1 * | 9/2007 | Makower ....................... | 600/424 |
| 2007/0225553 | A1 * | 9/2007 | Shahidi .......................... | 600/103 |

(Continued)

FOREIGN PATENT DOCUMENTS

| | | |
|---|---|---|
| EP | DE102005056080 A1 | 5/2007 |
| JP | 05285087 A | 11/1993 |

*Primary Examiner* — Anhtuan T Nguyen
*Assistant Examiner* — William Chou
(74) *Attorney, Agent, or Firm* — Schiff Hardin LLP

(57) ABSTRACT

In an imaging method for medical diagnostics and a device operating according to this method, during an endoscopic examination of a body region of a patient with an endoscope, an image is generated with a non-endoscopic imaging method and the image field of the endoscope is determined and rendered in the image (28) with accurate position and orientation.

13 Claims, 2 Drawing Sheets

(56) References Cited

U.S. PATENT DOCUMENTS

| | | | |
|---|---|---|---|
| 2007/0265518 A1 | 11/2007 | Boese et al. | |
| 2008/0243142 A1* | 10/2008 | Gildenberg | 606/130 |
| 2008/0269596 A1* | 10/2008 | Revie et al. | 600/424 |
| 2008/0281181 A1* | 11/2008 | Manzione et al. | 600/407 |
| 2008/0287805 A1* | 11/2008 | Li | 600/471 |
| 2012/0147359 A9* | 6/2012 | Stetten et al. | 356/73 |
| 2012/0253515 A1* | 10/2012 | Coste-Maniere et al. | 700/250 |
| 2013/0144116 A1* | 6/2013 | Cooper et al. | 600/102 |

\* cited by examiner

FIG 2
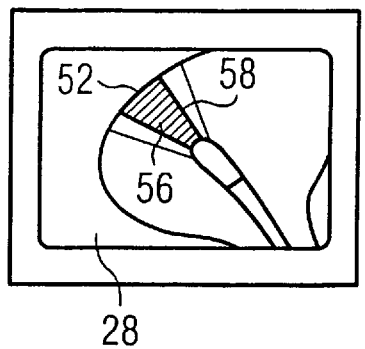
28
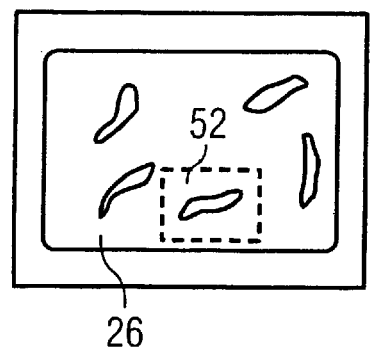
26
FIG 3
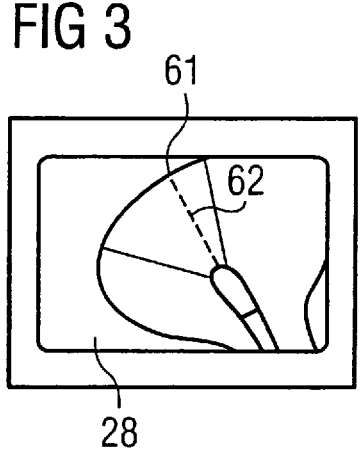
28
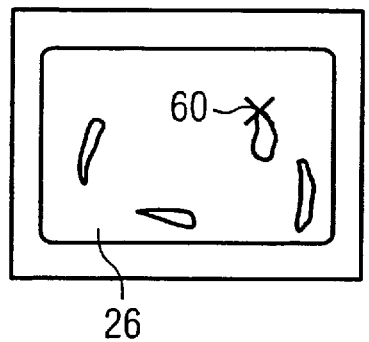
26
FIG 4
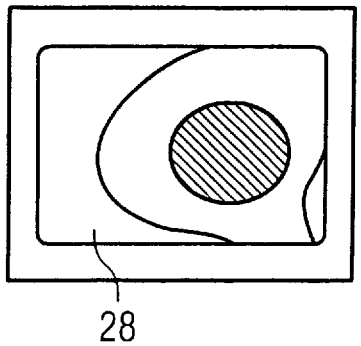
28
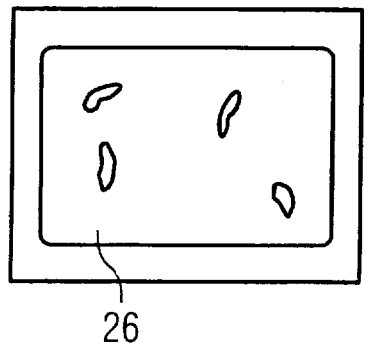
26

IMAGING METHOD FOR MEDICAL DIAGNOSTICS AND DEVICE OPERATING ACCORDING TO THIS METHOD

BACKGROUND OF THE INVENTION

1. Field of the Invention

The invention concerns an imaging method for medical diagnostics as well as an imaging device operating according to this method.

2. Description of the Prior Art

In medical diagnostics, in a series of application cases different imaging methods are used simultaneously or successively in order to facilitate the diagnosis or to avoid misdiagnoses. For example, in urology it is known to implement both an endoscopic examination and an x-ray examination. In an endoscopic method, high-resolution, color, optical images are generated in real time in the viewing direction of the endoscope. Each image, however, offers only two-dimensional information of the state of a section of the inner surface of the cavity and no information from deeper slices or in other viewing directions. In an x-ray method, information is also acquired from regions that are not visible in an endoscopy image. The linking of individual or multiples endoscopic images with one or more x-ray images of the same body require on the part of the observer not only a precise knowledge of the anatomy but also a developed three-dimensional spatial sense that must first be learned and frequently leads to misinterpretations. Moreover, pathological structures often deviate in a complex manner from the standard, such that a linking of endoscopy images and x-ray images is made more difficult.

One of the causes for these difficulties is that the methods normally used in addition to endoscopy (for example magnetic resonance methods or ultrasound methods in addition to the aforementioned x-ray methods) provide slice images of the examination subject, while in an endoscopy image only a boundary surface between an optically permeable medium and an optically impermeable medium is presented on a two-dimensional image plane.

SUMMARY OF THE INVENTION

An object of the present invention is to provide an imaging method for medical diagnostics that makes the interpretation of image data acquired with endoscopic methods and non-endoscopic methods easier for the user. A further object of the invention is to provide a device operating according to such a method.

The object according to the invention is achieved by an imaging method wherein, during an endoscopic examination of a body region of a patient, an image is generated of the body region with a non-endoscopic imaging method, and the image field of the endoscope is determined and rendered in the image with accurate position and orientation.

Via this measure it is possible for the user to associate the structures identified in the endoscopy image or in the image with one another and to assess them with regard to their diagnostic relevance.

In the present specification the term "image" is used exclusively for images that have been generated with a non-endoscopic imaging method, for example x-ray images, magnetic resonance images or ultrasound images.

A particularly simple determination of the position and orientation of the image field of the endoscope is possible via comparison of the image of the endoscope generated with the non-endoscopic imaging method (i.e. the endoscope rendered in the image) with a stored three-dimensional model of the endoscope for the non-endoscopic method. This model is a three-dimensional image of the endoscope that has been generated with this method in a calibration. In such a model comparison, the model is rotated and displaced (shifted) with corresponding coordinate transformations until the image of the endoscope and the model projected on the image plane after the coordinate transformations show maximal correlation. The image field of the endoscope (which is projected in the image plane just like the model) is also linked with the model.

As an alternative, the image coordinates of the image are determined in a fixed coordinate system and the position and orientation of the image field of the endoscope is measured in this fixed coordinate system with a position detection device. Due to this measure a model comparison is unnecessary and the image field can be projected into the image purely by calculation even if the endoscope itself is not visible in the image.

The association of a structure rendered in the endoscopy image with a structure rendered in the image is made easier for the observer if the rendered image field is bounded by optically impermeable structures recognizable in the image.

An additional facilitation for the user is achieved when a marker placed by the user in the endoscopy image is displayed in the image as a ray beam emanating from the endoscope or as an end point at an optically impermeable structure.

As an alternative or in addition, an area selected by the user in the endoscopy image is displayed in the image as a beam emanating from the endoscope or as an end surface at an optically impermeable structure.

In an embodiment of the invention, the marker or surface is automatically segmented with methods of image processing.

If the image generated with a non-endoscopic imaging method is a 3D image, the image field of the endoscope can be visualized particularly vividly in spatial representation.

A device according to the invention implements the method and achieves advantages that correspond to the advantages specified with regard to the method.

BRIEF DESCRIPTION OF THE DRAWINGS

FIGS. 2 through 4 respectively show an image of an examination subject generated with a non-endoscopic imaging method, and an endoscopy image.

DESCRIPTION OF THE PREFERRED EMBODIMENTS

Figure 1:
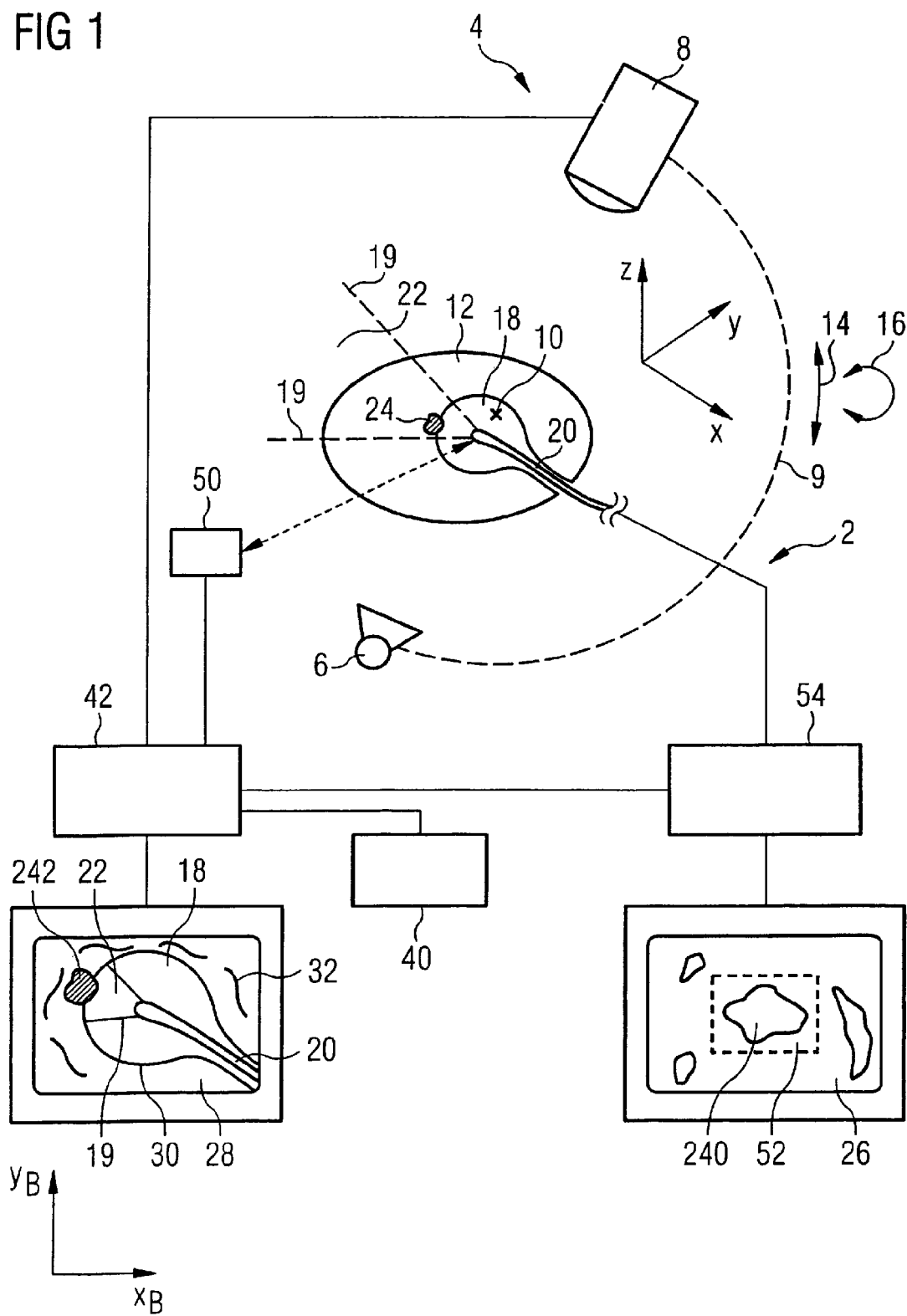
FIG. 1 schematically illustrates a device according to the invention.

As shown in FIG. 1, a device according to the invention has an endoscopy apparatus 2 as well as an image generation system 4 operated according to a non-endoscopic method, in the example a C-arm x-ray apparatus with an x-ray source 6 and an x-ray receiver 8 that are arranged on a C-arm 9 (shown in dashes in the Figure). The C-arm 9 can be pivoted around an isocenter 10 such that a two-dimensional image (slice image) can be generated from a body region of a patient 12. This pivot movement around an axis perpendicular to the plane spanned by the C-arm 9 (the plane of the drawing in FIG. 1) is illustrated by a double arrow 14. Moreover, if the C-arm 9 can be pivoted around an axis that lies in the plane spanned by it and is illustrated by the double arrow 16, it is possible to also generate a 3D image data set from the body region of the patient 12.

An endoscope 20 with which it is possible to optically observe a section of the internal surface of a wall 30 of a cavity 18 is inserted via a bodily orifice into said cavity 18 of the body 12. The lateral edge 19 of an image field 22 acquired by the endoscope 20 is drawn in dashes in FIG. 1.

Starting from the wall 30 of the cavity 18, in the example a pathological tissue zone 24 (for example a tumor) extends into a region lying behind the wall 30 (i.e. outside of the cavity 18). In the shown example this pathological tissue zone 24 lies in the image field 22 of the endoscope 20 and is recognizable as a planar structure 240 of the inner surface in an endoscopy image 26 acquired in this position of the endoscope 20, which planar structure 240 is in fact emphasized relative to the surroundings but whose unambiguous assessment is not possible without further measures.

Among other things, the contour of the wall 30 of the cavity 18 (which contour forms an optically impermeable structure) as well as further structures 32 situated in the slice plane are recognizable in a non-endoscopic image 28 (in the example a two-dimensional x-ray slice image) generated with the image generation system 4. A structure 242 that extends into the tissue and that reflects pathological tissue zones 24 is now recognizable for the user in this image 28. Moreover, the endoscope 20 is visible in the image 28 in the shown exemplary embodiment.

Using a three-dimensional model of the endoscope 20 stored in a memory 40 of the image generation system 4, the position of the endoscope 20 (and therefore of the image field 22) relative to an image coordinate system $x_B$, $y_B$ associated with the image generation system 4 is now determined by comparison of the image of the endoscope 20 with this model. The image field 22 is mixed into the image 28 with accurate position and orientation (i.e. is visibly emphasized for the user) with an image processing software implemented in a control and evaluation device 42 of the image generation system 4. For example, the entire image field 22 is colored for this purpose. Alternatively, it is also possible to exclusively display the edge 19 of the image field 22 as boundary rays in the image 28.

Moreover, in the shown example both the edge 19 and the image field 22 end at the contour (recognizable in the image 28) of the wall 30 of the cavity 18 in order to visualize to the observer that only a surface region corresponding to this contour is visible in the endoscopy image 26. Alternatively or additionally, it is possible to emphasize the end surface of the image field 22 at the optically impermeable structure (wall 30).

By comparison of endoscopy image 26 and image 28, the observer now recognizes that the flat structure 240 visible in the endoscopy image 26 belongs to the structure 242 extending deep into the tissue in image 28, and the observer can in this manner now clearly associate both structures 240, 242 with one another and, for example, better assess their volume extent since the endoscopy image 26 and the image 28 impart size impressions in slice planes perpendicular to one another.

Moreover, in the shown example a position detection device 50 is associated with the endoscope 20, with which position detection device 50 the position and orientation of the endoscope 20 (and therefore also the position and orientation of the image field 22) can be determined in a fixed coordinate system x, y, z with the use of sensors (not shown in the Figure) arranged in the region of the endoscope tip. Given a known relationship between the image coordinate system $x_B$, $y_B$ of the image 28 and the fixed coordinate system x, y, z, it is possible to enter the image field 22 into the image 28 with correct position without it being necessary to store a model of the endoscope 20.

The observer now has the possibility to mark an area of interest to him or her in the endoscopy image, which area encompasses the structure 240 in the example. This area 52 is relayed from a control and evaluation device 54 of the endoscopy apparatus 2 to the control and evaluation device 42 of the image generation system 4 and is mixed into the image 28 with the image processing software, for example in the form of a limited image field 56 shown in hatching or in the form of boundary rays 58 drawn in dashes, as is illustrated in FIG. 2.

As an alternative to this, the observer can also place a marker 60 at a single point of interest to the observer, which marker 60 is then shown either as a sight line or ray 62 (drawn in dashes) ending at the wall 30 or likewise as an end point 61 of this ray 62 at the wall 30, i.e. the optically impermeable structure in the image 28.

However, in principle it is also possible that the area 52 of interest or the marker is automatically segmented with methods of image processing.

Situations in which the endoscope 20 is visible in the image (slice image) are presented in FIGS. 1 through 3. This is not necessarily the case since the tip of the endoscope can also be located in a plane lying outside of the slice plane.

A situation in which the tip of the endoscope is arranged outside of the plane of the drawing (the image plane of image 28) shown in FIG. 1 and the optical axis of the video camera integrated into the endoscope is aligned perpendicular to the slice plane is presented in FIG. 4. In this case the image field 22 of the endoscope is a circular area (an ellipse given angled orientation of the optical axis) and the observer can in any case learn the information that a synthesis of the two images is not possible upon consideration of the image of the endoscopy image 26 and the image 28.

In the exemplary embodiment, two-dimensional slice images are generated by an image generation system 4. However, the method can be used with particularly great advantage even when the image generation system 4 generates a three-dimensional image data set of the examination subject 12. Then the normally conical image field 22 of the endoscope can be spatially mixed into the 3D data set and the orientation of the user is significantly facilitated.

The invention is also not limited to the flexible endoscope depicted in the exemplary embodiment. In principle the endoscope can also be executed rigidly or as an endoscopy capsule.

Although modifications and changes may be suggested by those skilled in the art, it is the intention of the inventors to embody within the patent warranted hereon all changes and modifications as reasonably and properly come within the scope of their contribution to the art.

We claim as our invention:

1. An imaging method for medical diagnostics, comprising the steps of:
    implementing an endoscopic examination of a body region of a subject using an endoscope and, with said endoscope, obtaining an endoscopic image;
    in real time during the endoscopic examination, operating a non-endoscopic imaging apparatus to produce real time non-endoscopic image data using a non-endoscopic imaging method and, generating a real time non-endoscopic image of the body region in real time during the endoscopic examination from said real time non-endoscopic image data;
    automatically determining an image field of the endoscope in which said endoscopic image is obtained;
    displaying the determined image field of the endoscope in a display of the real time non-endoscopic image with a correct position and orientation corresponding to the position and orientation of the endoscope; and automatically demarcating a region of interest in said image field of said endoscope displayed in the display of the real time non-endoscopic image.

2. An imaging method for medical diagnosis as claimed in claim 1 comprising storing a three-dimensional model of the endoscope and, in said non-endoscopic imaging method, determining the position and orientation of the image field of the endoscope by comparing the stored three-dimensional model of the endoscope with a real time image of the endoscope generated with the non-endoscopic imaging method.

3. An imaging method for medical diagnosis as claimed in claim 1 comprising determining image coordinates of the real time non-endoscopic image of the body region in a fixed coordinate system, and determining the position and orientation of the image field of the endoscope in said fixed coordinate system using a position detector.

4. An imaging method for medical diagnosis as claimed in claim 1 comprising defining said image field using optically impermeable structures that are recognizable in said real time non-endoscopic image.

5. An imaging method for medical diagnosis as claimed in claim 1 comprising placing a marker in a display of the endoscopic image defining a ray emanating from the endoscope or an end point at an optically impermeable structure.

6. An imaging method for medical diagnosis as claimed in claim 5 comprising segmenting the marker or the optically impermeable structure by image processing.

7. An imaging method for medical diagnosis as claimed in claim 1 comprising defining an area in a display of the endoscopic image as a beam emanating from the endoscope or as an end surface at an optically impermeable structure.

8. An imaging method for medical diagnosis as claimed in claim 7 comprising segmenting the marker or the optically impermeable structure by image processing.

9. An imaging method for medical diagnosis as claimed in claim 1 comprising generating said real time non-endoscopic image as a three-dimensional image.

10. An imaging method for medical diagnosis as claimed in claim 1 comprising generating said non-endoscopic image as an x-ray image.

11. An imaging device for medical diagnostics, comprising:

an endoscope configured to implement an endoscopic examination of a body region of a subject, said endoscope having an image field associated therewith in which, in said endoscopic examination, said endoscope is configured to obtain an endoscopic image;

a non-endoscopic imaging system configured to produce real time non-endoscopic data in real time during said endoscopic examination and to generate a real time non-endoscopic image of the body region during said endoscopic examination using said real time non-endoscopic data;

a computer configured to automatically determine an image field of the endoscope in which said endoscopic image is obtained;

said computer being configured to render the determined image field of the endoscope in the real time non-endoscopic image with a correct position and orientation corresponding to the position and orientation of the endoscope;

a display connected to said computer at which said computer is configured to cause said real time non-endoscopic image to be visually presented with said image field of said endoscope therein at said correct position and orientation; and said computer being configured to automatically determine a region of interest and to visually show said region of interest in said image field of said endoscope in the visual presentation of said real time non-endoscopic image at said display.

12. An imaging device as claimed in claim 11 wherein said non-endoscopic image generating system is a C-arm x-ray apparatus.

13. An imaging device as claimed in claim 11 comprising a position detection device physically associated with the endoscope and configured to detect the position of the endoscope in a fixed coordinate system, and to provide said computer with an electronic signal representing said position of the endoscope in said fixed coordinate system.

* * * * *